US008697092B2

(12) United States Patent
Cox et al.

(10) Patent No.: US 8,697,092 B2
(45) Date of Patent: Apr. 15, 2014

(54) **IDENTIFICATION OF A CONSERVED INNER CORE OLIGOSACCHARIDE OF *MORAXELLA CATARRHALIS* LIPOPOLYSACCHARIDE AS A VACCINE ANTIGEN**

(76) Inventors: Andrew D. Cox, Ottawa (CA); James C. Richards, Ottawa (CA)

( * ) Notice: Subject to any disclaimer, the term of this patent is extended or adjusted under 35 U.S.C. 154(b) by 0 days.

(21) Appl. No.: 13/056,165

(22) PCT Filed: Sep. 4, 2009

(86) PCT No.: PCT/CA2009/001193
§ 371 (c)(1), (2), (4) Date: Mar. 15, 2011

(87) PCT Pub. No.: WO2010/025541
PCT Pub. Date: Mar. 11, 2010

(65) Prior Publication Data

US 2011/0165163 A1 Jul. 7, 2011

Related U.S. Application Data

(60) Provisional application No. 61/094,098, filed on Sep. 4, 2008.

(51) Int. Cl.
*A61K 39/02* (2006.01)
*A61K 39/385* (2006.01)
*A01N 43/04* (2006.01)
*C07H 1/00* (2006.01)

(52) U.S. Cl.
USPC ................ 424/251.1; 424/197.11; 424/193.1; 424/234.1; 514/23; 536/123.1

(58) Field of Classification Search
None
See application file for complete search history.

(56) References Cited

U.S. PATENT DOCUMENTS

| | | | |
|---|---|---|---|
| 6,685,949 | B1 | 2/2004 | Gu et al. |
| 2006/0062741 | A1 | 3/2006 | Gu |

OTHER PUBLICATIONS

Peak et al. FEBS J. 274: 2024-2037, 2007—Epub Mar. 27, 2007.*
Pollack et al. J. Clin. Invest. 79: 1421-1430, 1987.*
Edwards et al (May 2005), J. Bacter. 187(9),pp. 2939-2947 Characterization of a cluster of three glycosyltransferase enzymes essential for *Moraxella catarrhalis* lipooligosaccharide assembly.
Gu et al (May 1998) Infect. Immun. 66(5), pp. 1891-1897 Synthesis and Characterization of Lipoligosaccharide-based conjugates as vaccine candidates for *Moraxella* (Branhamella) *catarrhalis*.
Yu et al (May 2005) Infect. Immun.73 (5) pp. 2790-2796 Synthesis and characterization of lipooligosaccharide based conjugate vaccines for serotype B *Moraxella catarrhalis*.
Yu et al (Jun. 2007) Infect.Immun 75 (6) pp. 2974-2980 Biological and Immunological characteristics of lipooligosaccharide based conjugate vaccines for serotype C *Moraxella catarrhalis*.
McMichael (2001) Vaccine 19 pp. S101-S107 Vaccines for *Moraxella catarrhalis*.
Schwingel et al (Mar. 12, 2008) glycobiology 18(6) pp. 447-455 A unique glycosyltransferase involved in the initial assembly of *Moraxella catarrhalis* lipooligosaccharides.
Raina T. Gergova et al: “Bactericidal Monoclonal Antibody Against *Moraxella catarrhalis* Lipooligosaccharide Cross-Reacts with *Haemophilius* Spp”, Current Microbiology, Springer-Verlag, NE, vol. 54, No. 2, Jan. 5, 2007, pp. 85-90, ISSN: 1432-0991.
C.M. Verduin et al: “*Moraxella catarrhalis*: from Emerging to Established Pathogen”, Clinical Microbiology Reviews, vol. 15, No. 1, Jan. 1, 2002, pp. 125-144, ISSN: 0893-8512.
Andrew D Cox et al: “Investigating the Potential of Conserved Inner Core Oligosaccharide Regions of Lipopolysaccharide as Vaccine Antigens: Accessibility and Functional Activity of Monoclonal Antibodies and Glycoconjugate derived sera”, Glycoconjugate Journal, Kluwer Academic Publishers, BO,vol. 28, No. 3-4, May 18, 2011, pp. 165-182, ISSN: 1573-4986.

* cited by examiner

*Primary Examiner* — S. Devi
(74) *Attorney, Agent, or Firm* — Michael R. William; Ade & Company Inc

(57) ABSTRACT

There are disclosed herein antigenic structures useful in producing vaccines against and compounds helpful in combating diseases caused by the bacterium *Moraxella catarrhalis*. Disclosed are specific structures of the carbohydrate molecules derived from genetically engineered strains of *Moraxella catarrhalis*, which when presented appropriately to the immune system will facilitate a functional immune response to the target core oligosaccharide region.

6 Claims, 7 Drawing Sheets

| Bacterial Strain | Primary mAb (Isotype) | Secondary Antibody PE labelled | |
|---|---|---|---|
| M.Cat Igt2 | - | - |  |
| M.cat Igt2 | Isotype Control Mouse IgG2b | Goat-anti Mouse IgG2b-PE |  |
| M.cat Igt2 | MC-2-1 (IgG2b) | Goat-anti Mouse IgG2b-PE |  |
| M.cat WT Serotype A | MC-2-1 (IgG2b) | Goat-anti Mouse IgG2b-PE |  |
| L3galE | MC-2-1 (IgG2b) | Goat-anti Mouse IgG2b-PE |  |

IDENTIFICATION OF A CONSERVED INNER CORE OLIGOSACCHARIDE OF *MORAXELLA CATARRHALIS* LIPOPOLYSACCHARIDE AS A VACCINE ANTIGEN

PRIOR APPLICATION INFORMATION

This application claims the benefit of U.S. Provisional Patent Application 61/094,098, filed Sep. 4, 2008.

BACKGROUND OF THE INVENTION

*Moraxella catarrhalis* can cause otitis media which is of significant public health and economic concern in humans. Vaccine strategies are being pursued to combat these infections. These strategies are based on the identification of conserved, immunogenic cell surface components; however, the detection of conserved molecules that would confer protection against the vast majority of strains from a single species has proven problematic.

The outer leaflet of the outer membrane of all Gram-negative bacteria contains an amphiphillic carbohydrate molecule termed lipopolysaccharide (LPS).

An O-antigenic polymeric repeating unit (O-antigen) can be present or absent beyond the core oligosaccharide of the LPS molecule and is absent in all strains of *Moraxella catarrhalis* so far examined. The core oligosaccharide can be arbitrarily divided into an outer and inner core and is connected to the lipid A region via one or more ketose sugar(s), 2-keto-3-deoxy-octulosonic acid (Kdo). The lipid A region is responsible for the endotoxic activity of the Gram-negative bacterium and consists in most species of a disaccharide of glucosamine sugars that are phosphorylated and contain both ester and amide linked fatty acids. The outer core region can be somewhat variable within a species and is therefore not a good vaccine candidate. However what is arbitrarily termed the inner core oligosaccharide has been found to be conserved within several species, and is the vaccine antigen of choice in this application.

The endotoxicity of the lipid A region is due to the fatty acid residues. Removal of the ester-linked fatty acids leaves an O-deacylated LPS species that is no longer endotoxic. Removal of all fatty acids i.e. both the amide and ester-linked fatty acids can be performed chemically, but involves harsh conditions which can sometimes affect other regions of the LPS molecule if residues susceptible to these conditions are elaborated by the bacterial species LPS of interest. Therefore if a conserved residue is removed by the conditions employed to prepare the vaccine antigen, it is likely that the resulting immune response to that antigen would not be broadly cross reactive or protective. We have previously detailed the utilisation of amidases from *Dictyostelium discoideum* to remove the N-linked fatty acids and thus avoid the use of harsh chemical conditions (and the possible removal of sensitive residues).

LPS based vaccines generally require the removal of sufficient fatty acids from the lipid A region of the molecule to preclude endotoxicity and to derive a molecule that is amenable to conjugation strategies.

Current strategies used in the art to prepare LPS-based glycoconjugate vaccines link the carbohydrate to a carrier protein either via the Kdo residues of O-deacylated LPS or of core oligosaccharides or via the derived lipid A region of the molecule. We have shown previously that conjugation via the Kdo residues does not optimally present the target core oligosaccharide region to the host's immune system and the resulting sera are not functional.

SUMMARY OF THE INVENTION

According to a first aspect of the invention, there is provided a reagent for inducing an immune response comprising a purified or isolated inner core oligosaccharide (OS) having the general formula of:

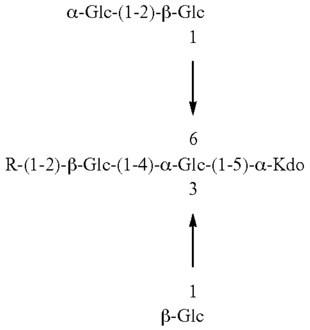

where R is hydrogen or 2-acetamido-2-deoxy-D-α-glucopyranose (GlcNAc), 'Kdo' is 2-keto-3-deoxy-octulosonic acid and 'Glc' is glucose.

According to a second aspect of the invention, there is provided a vaccine capable of eliciting an immune response against at least one bacterial strain of the species *Moraxella catarrhalis* comprising a purified or isolated inner core oligosaccharide (OS) having the general formula of;

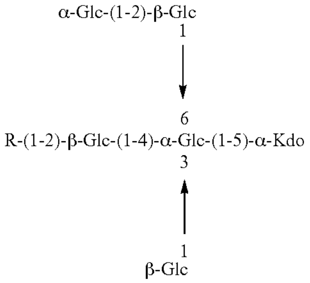

where R is hydrogen or 2-acetamido-2-deoxy-D-α-glucopyranose (GlcNAc), 'Kdo' is 2-keto-3-deoxy-octulosonic acid and 'Glc' is glucose.

According to a third aspect of the invention, there is provided a method of preparing a medicament for the treatment or prevention of a disease caused by *Moraxella catarrhalis* infection comprising mixing a purified or isolated inner core oligosaccharide (OS) having the general formula of:

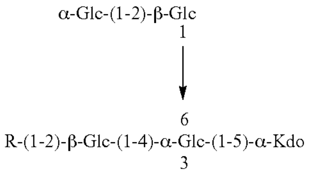

-continued

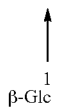

where R is hydrogen or 2-acetamido-2-deoxy-D-α-glucopyranose (GlcNAc), 'Kdo' is 2-keto-3-deoxy-octulosonic acid and 'Glc' is glucose with a suitable immunogenic presenting agent.

According to a fourth aspect of the invention, there is provided a method of treating a disease caused by *Moraxella catarrhalis* infection comprising administering to an individual in need of such treatment a purified or isolated inner core oligosaccharide (OS) having the general formula of:

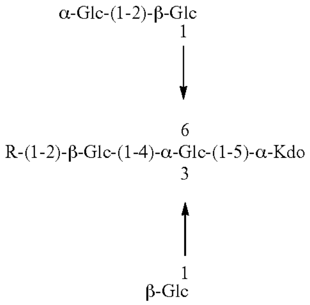

where R is hydrogen or 2-acetamido-2-deoxy-D-α-glucopyranose (GlcNAc), 'Kdo' is 2-keto-3-deoxy-octulosonic acid and 'Glc' is glucose and a suitable immunogenic presenting agent.

According to a fifth aspect of the invention, there is provided a purified or isolated inner core oligosaccharide (OS) having the general formula of:

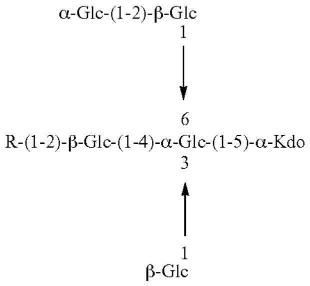

where R is hydrogen or 2-acetamido-2-deoxy-D-α-glucopyranose (GlcNAc), 'Kdo' is 2-keto-3-deoxy-octulosonic acid and 'Glc' is glucose.

According to a further aspect of the invention, there is provided an isolated lipopolysaccharide derived moiety consisting essentially of a conserved penta-glucosyl inner core moiety free of variable outer core oligosaccharide extensions.

According to a further aspect of the invention, there is provided an isolated lipopolysaccharide derived moiety consisting essentially of a conserved penta-glucosyl inner core moiety having the structure I

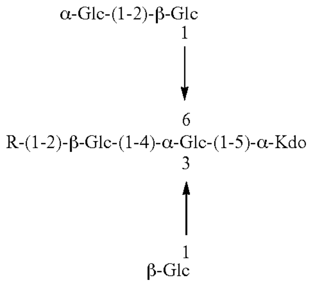

where R is hydrogen or 2-acetamido-2-deoxy-D-α-glucopyranose (GlcNAc), 'Kdo' is 2-keto-3-deoxy-octulosonic acid and 'Glc' is glucose.

According to another aspect of the invention, there is provided a pharmaceutical composition for eliciting functional antibodies comprising the isolated lipopolysaccharide moiety described above.

According to a further aspect of the invention, there is provided a method for the production and harvesting of a functional cross-reactive antibody against *Moraxella catarrhalis* which comprises: (a) generating antibodies to the lipopolysaccharide moiety described above; (b) testing said antibodies against a plurality of *Moraxella catarrhalis* strains; and (c) selecting those antibodies which are cross-reactive.

According to another aspect of the invention, there is provided the use of the composition described above for the preparation of a medicament for treating a disease caused by infection with *Moraxella catarrhalis.*

According to another aspect of the invention, there is provided a glycoconjugate comprising: a lipopolysaccharide moiety consisting essentially of a penta-glucosyl inner-core moiety having the structure I

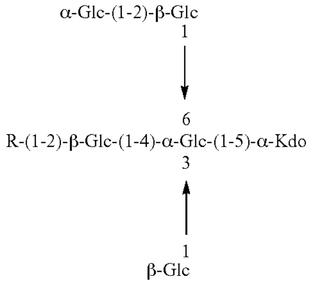

where R is hydrogen or 2-acetamido-2-deoxy-D-α-glucopyranose (GlcNAc), 'Kdo' is 2-keto-3-deoxy-octulosonic acid and 'Glc' is glucose and an immunogenic carrier.

Figure 5:
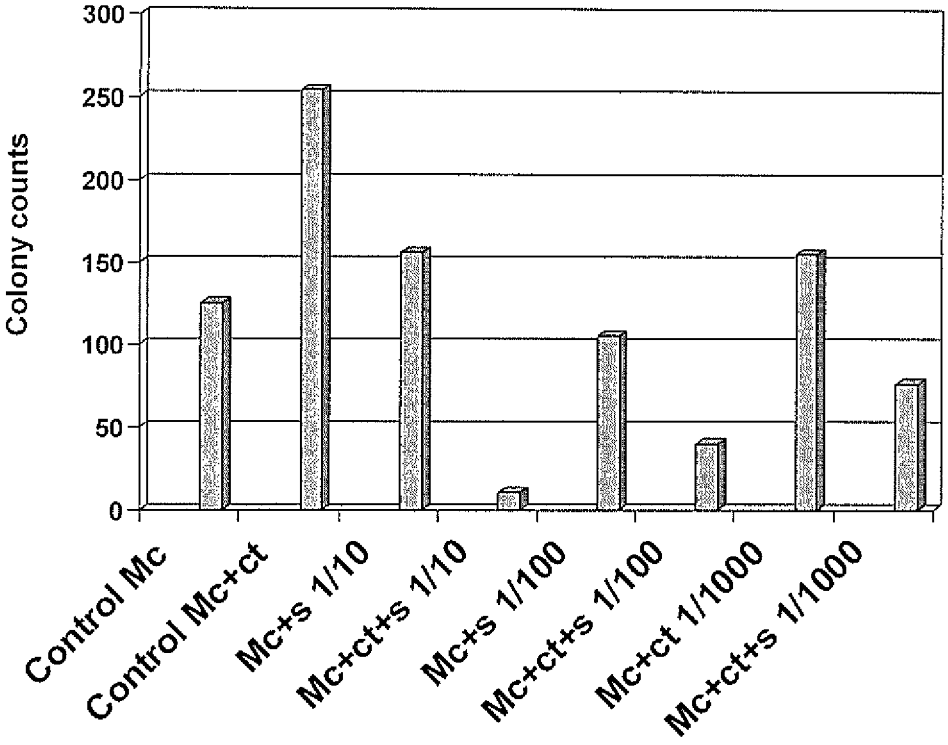

*typhimurium* (S. thy), *Mannheimia haemolytica* (Mh), *Haemophilus influenzae* (Hi) and *Neisseria meningitidis* (Nm.) at dilution as indicated FIG. 5. Graph of colony counts of *Moraxella catarrhalis* following bactericidal assay. Mc is *Moraxella catarrhalis*; ct is complement; s is mAb MC2-1.

Figure 6:
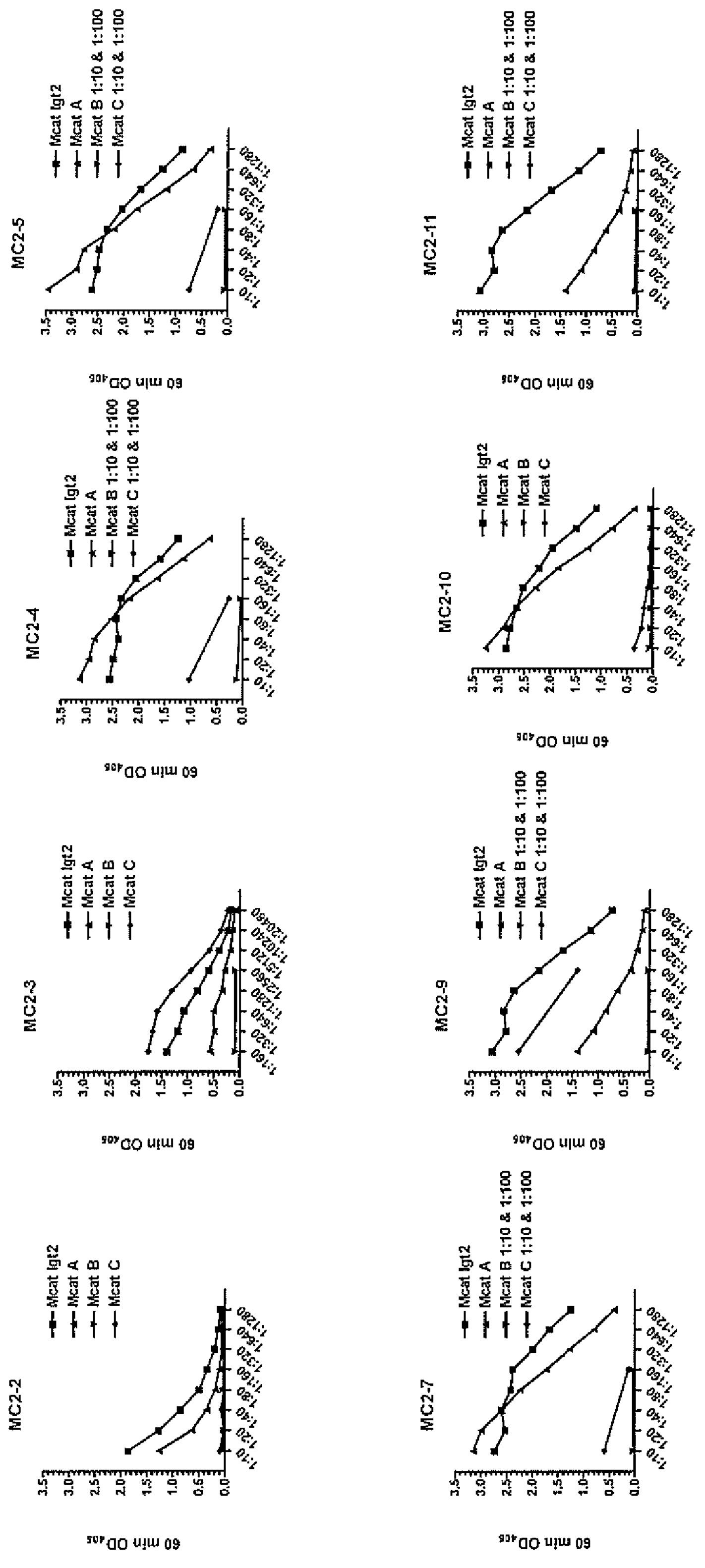

FIG. 6. Titration curves of LPS ELISA with mAbs 2-2, -3, -4, -5, -7, -9, -10 and -11 against LPS from wt strains serotypes A, B and C and the lgt2 mutant of serotype A.

Figure 7:
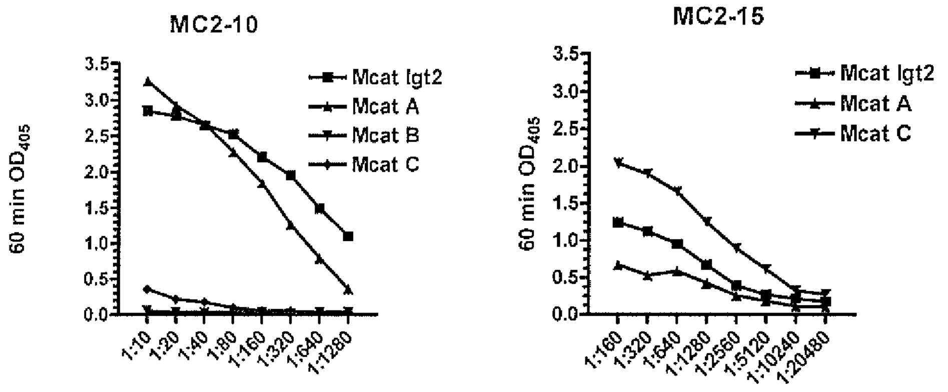

FIG. 7. Titration curves of LPS ELISA with mAbs 2-10 and -15 against LPS from wt strains serotypes A and C and the lgt2 mutant of serotype A.

Figure 8:
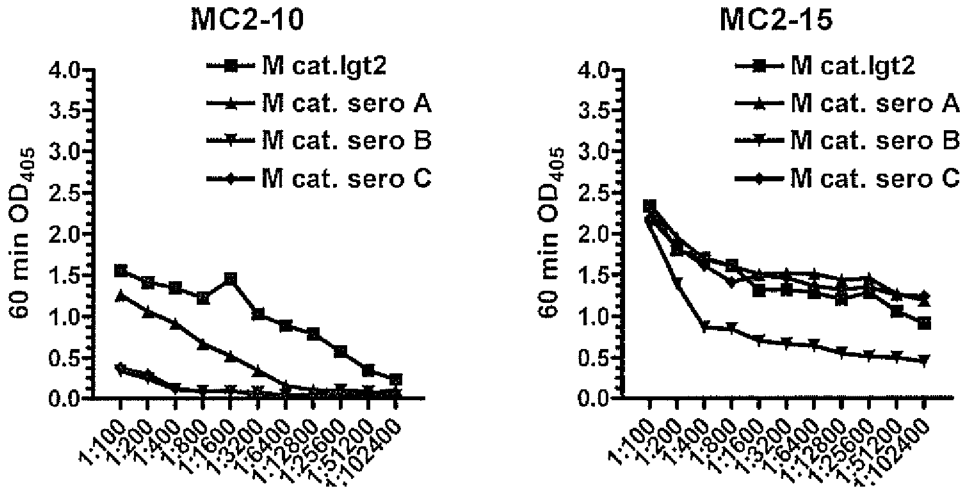

FIG. 8. Titration curves of whole cell ELISA with mAbs 2-10 and -15 against whole cells from wt strains serotypes A, B and C and the lgt2 mutant of serotype A.

Figure 9:
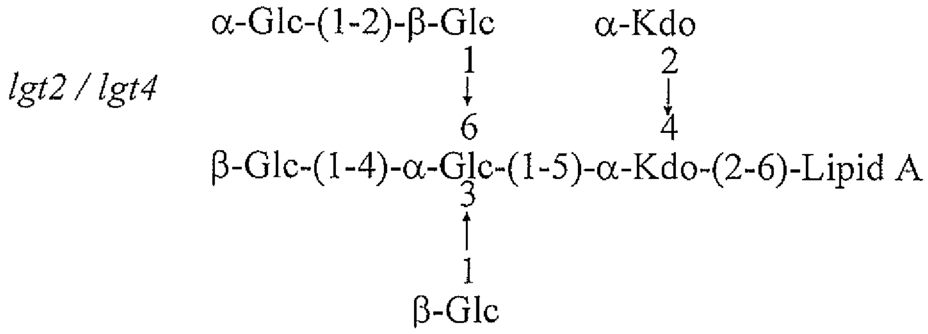

FIG. 9 Structure of the LPS from the lgt2/lgt4 double mutant of serotype A strain of *Moraxella catarrhalis*

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

There are disclosed herein antigenic structures useful in producing vaccines against and compounds helpful in combating diseases caused by the bacterium *Moraxella catarrhalis*.

Disclosed are specific structures of the carbohydrate molecules derived from genetically engineered strains of *Moraxella catarrhalis*, which when presented appropriately to the immune system will facilitate a functional immune response to the target core oligosaccharide region.

In one aspect, the invention is directed to a purified or isolated core oligosaccharide structure selected from the group consisting of:

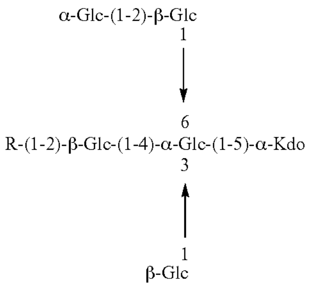

where R is H or α-GlcNAc (2-acetamido-2-deoxy-D-α-glucopyranose), 'Kdo' is 2-keto-3-deoxy-octulosonic acid and 'Glc' is glucose.

As will be appreciated by one of skill in the art and as discussed above, such core oligosaccharide structures have many utilities in the art. For example, as discussed above, such structures may be used in the preparation of a vaccine for immunizing individuals in need of such treatment against disease(s) caused by *Moraxella catarrhalis.*

For example, in some embodiments, bacterial cells comprising a core oligosaccharide as described above may be treated by means known in the art, for example, heat-killing, or the core oligosaccharide may be purified and/or isolated by means known in the art and used for immunization purposes. As discussed above, bacterial strains producing such core oligosaccharide structures are exemplified above.

In another embodiment of the invention, there is provided a method of immunizing an individual against a *Moraxella* infection comprising administering to an individual in need of such treatment an effective amount of a core oligosaccharide as described above. As will be appreciated by one of skill in the art, such an immunization or vaccination or administration can also be considered a method of preventing a disease caused by *Moraxella* by administering to an individual in need of such treatment a core oligosaccharide as described above.

A reagent for inducing an immune response comprising a purified or isolated inner core oligosaccharide (OS) having the general formula of:

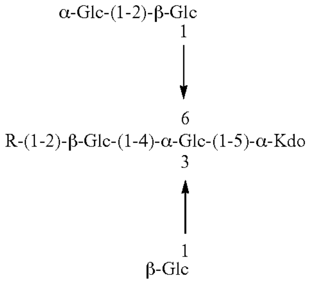

where R is hydrogen or 2-acetamido-2-deoxy-D-α-glucopyranose (GlcNAc), 'Kdo' is 2-keto-3-deoxy-octulosonic acid and 'Glc' is glucose.

In a preferred embodiment, as discussed herein, the reagent is capable of eliciting functional antibodies against at least one of the strains within the species of *Moraxella catarrhalis*, preferably against a majority of the strains within the species *Moraxella catarrhalis*. More preferably, the reagent is capable of eliciting functional antibodies against at least 60%, at least 70%, at least 80%, at least 85%, at least 90% or at least 95% of the strains within the species *Moraxella catarrhalis.*

As used herein, 'functional antibodies' refers to antibodies that for example recognize wild-type *Moraxella catarrhalis* LPS, *Moraxella catarrhalis* whole cells or have bactericidal activity against *Moraxella catarrhalis*, as discussed herein.

In some embodiments, the reagent further comprises an immunogenic presenting agent. As will be understood by one of skill in the art, 'an immunogenic presenting agent' refers to any agent which increases or improves the immunogenicity of the reagent and may be for example but by no means limited to an adjuvant, a carrier protein, liposomes or the like.

As used herein, 'immunogenic carrier' has the commonly used meaning in the art, that is, refers to a carrier protein or the like.

As discussed herein, in some embodiments, the inner core oligosaccharide is attached to lipid A.

As discussed herein, preferably, the inner core oligosaccharide is substantially free of outer core oligosaccharide.

As will be appreciated by one of skill in the art, the reagent may be used as a vaccine or in the preparation of a vaccine, as described herein.

For example, the reagent may be used in a method for preparing a medicament, for the treatment or prevention of a disease caused by *Moraxella catarrhalis* infection comprising mixing a purified or isolated inner core oligosaccharide (OS) having the general formula of:

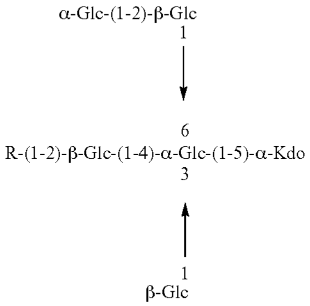

where R is hydrogen or 2-acetamido-2-deoxy-D-α-glucopyranose (GlcNAc), 'Kdo' is 2-keto-3-deoxy-octulosonic acid and 'Glc' is glucose with a suitable immunogenic presenting agent.

As will be appreciated by one of skill in the art, the medicament may be a vaccine. The vaccine may be a conjugated vaccine.

As will be readily apparent to one of skill in the art, the reagent or a vaccine prepared therefrom may be administered to an individual in need of such treatment, for example an individual suffering from, suspected of suffering from, or at risk of developing a *Moraxella catarrhalis* infection. Thus, the reagent may be administered to an individual known to be infected with or suspected of being infected with *Moraxella catarrhalis* as a means of stimulating an immune response. Alternatively, individuals at risk of developing a *Moraxella catarrhalis* infection or desirous of preventing a *Moraxella catarrhalis* infection may be protected against such infection by administering the reagent as described above or a vaccine prepared therefrom.

Accordingly, in another aspect of the invention, there is provided a method of treating a disease caused by *Moraxella catarrhalis* infection comprising administering to an individual in need of such treatment a purified or isolated inner core oligosaccharide (OS) having the general formula of:

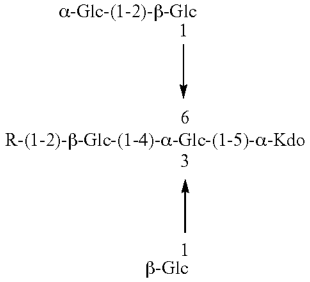

where R is hydrogen or 2-acetamido-2-deoxy-D-α-glucopyranose (GlcNAc), 'Kdo' is 2-keto-3-deoxy-octulosonic acid and 'Glc' is glucose and a suitable immunogenic presenting agent.

In a further aspect of the invention, there is provided a purified or isolated inner core oligosaccharide (OS) having the general formula of:

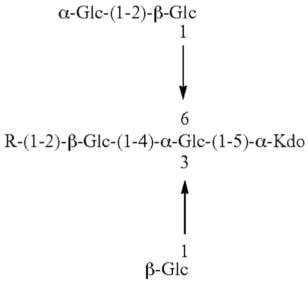

where R is hydrogen or 2-acetamido-2-deoxy-D-α-glucopyranose (GlcNAc), 'Kdo' is 2-keto-3-deoxy-octulosonic acid and 'Glc' is glucose. As will be appreciated by one of skill in the art, the purified or isolated inner core oligosaccharide may be derived from the inner core of *Moraxella catarrhalis* or a synthetic version thereof or a functional equivalent thereof.

As will be appreciated by one of skill in the art, the inner core oligosaccharide or a portion thereof is an epitope as discussed herein and may be used as the immunogenic component in a vaccine or medicament as discussed herein.

In a further aspect of the invention, there are provided antibodies reactive with the epitope, immunogenic component or reagent described above.

In a further aspect of the invention, there is provided a method for the identification of immunogenic epitopes of strains of a species of *Moraxella catarrhalis* comprising inoculating a suitable host organism with lgt2/lgt4 mutant strain of *Moraxella catarrhalis* and testing such antibodies against a wild type *Moraxella catarrhalis* strain to identify those antibodies which are reactive, and for which the epitopes are therefore accessible in the wild-type organism.

The invention also provides an isolated lipopolysaccharide derived moiety consisting essentially of a conserved penta-glucosyl inner core moiety free of variable outer core oligosaccharide extensions.

Preferably, the isolated lipopolysaccharide derived moiety consisting essentially of a conserved penta-glucosyl inner core moiety having the structure I

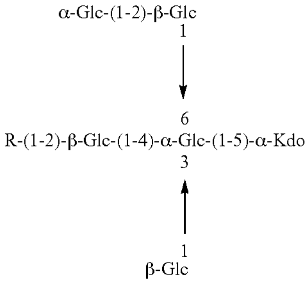

where R is hydrogen or 2-acetamido-2-deoxy-D-α-glucopyranose (GlcNAc), 'Kdo' is 2-keto-3-deoxy-octulosonic acid and 'Glc' is glucose.

There is also provided a method for the production and harvesting of a functional cross-reactive antibody against *Moraxella catarrhalis* which comprises: (a) generating antibodies to the lipopolysaccharide moiety described herein; (b) testing said antibodies against a plurality of *Moraxella catarrhalis* strains; and (c) selecting those antibodies which are cross-reactive.

There is also provided a glycoconjugate comprising: a lipopolysaccharide moiety consisting essentially of a penta-glucosyl inner-core moiety having the structure I

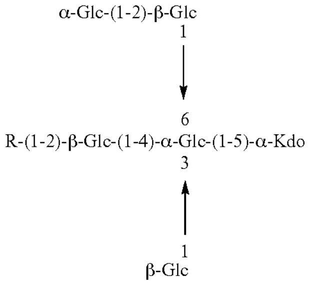

where R is hydrogen or 2-acetamido-2-deoxy-D-α-glucopyranose (GlcNAc), 'Kdo' is 2-keto-3-deoxy-octulosonic acid and 'Glc' is glucose and an immunogenic carrier. In the glycoconjugate, the lipopolysaccharide moiety and the immunogenic carrier may be cross-linked with a linker molecule. As will be appreciated by one of skill in the art, suitable linker molecules for such purposes are well known and may be selected by routine experimentation.

The identification, production and utilisation of conserved inner core regions of *Moraxella catarrhalis* LPS as a vaccine antigen will be described in the following examples. However, the invention is not necessarily limited by the examples.

Example 1

LPS Structures of *Moraxella catarrhalis*

Figure 1:
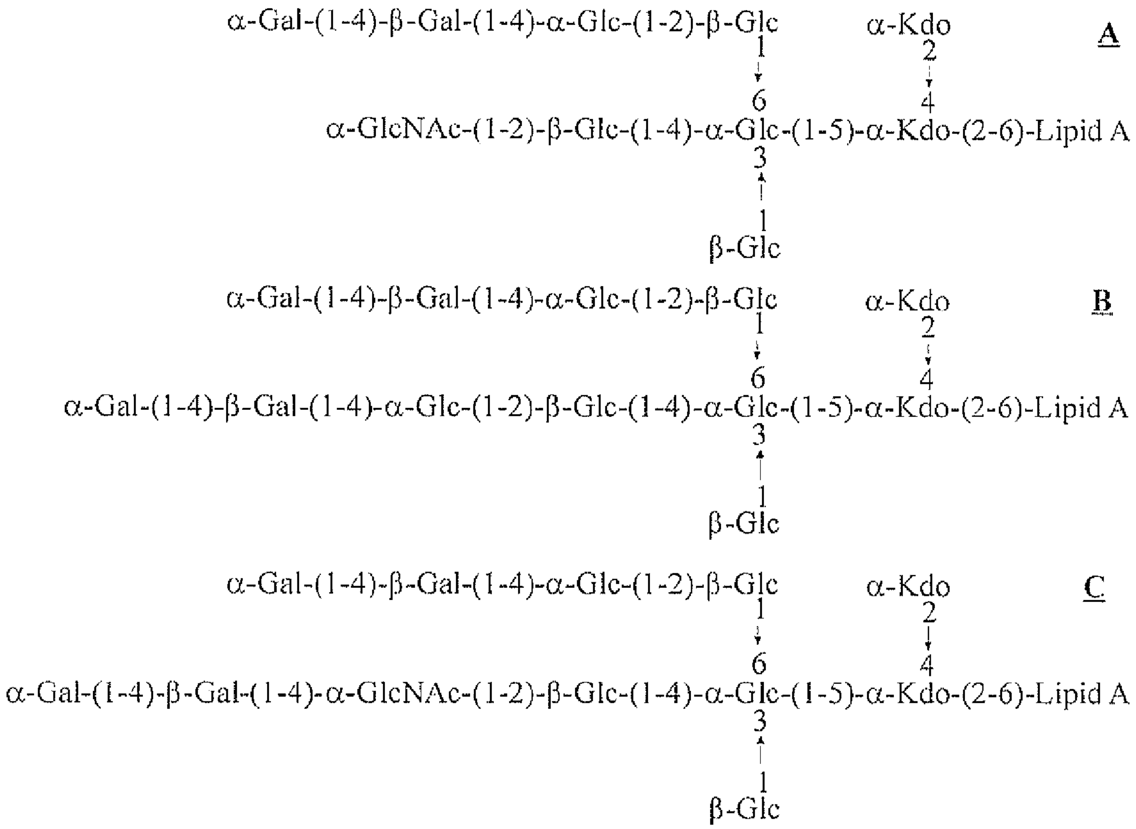
FIG. 1 Structures of the LPS from the 3 serotypes of *Moraxella catarrhalis*

*Moraxella catarrhalis* (Mc) can be classified into 3 serotypes (A, B, C) based upon LPS structure, shown in FIG. 1.

Mc LPS structure is rather unique amongst Gram-negative bacteria as it does not contain any heptose residues, but instead has glucose residues attached to the Kdo sugar, and indeed the initial glucose residue is tri-substituted.

Figure 2:
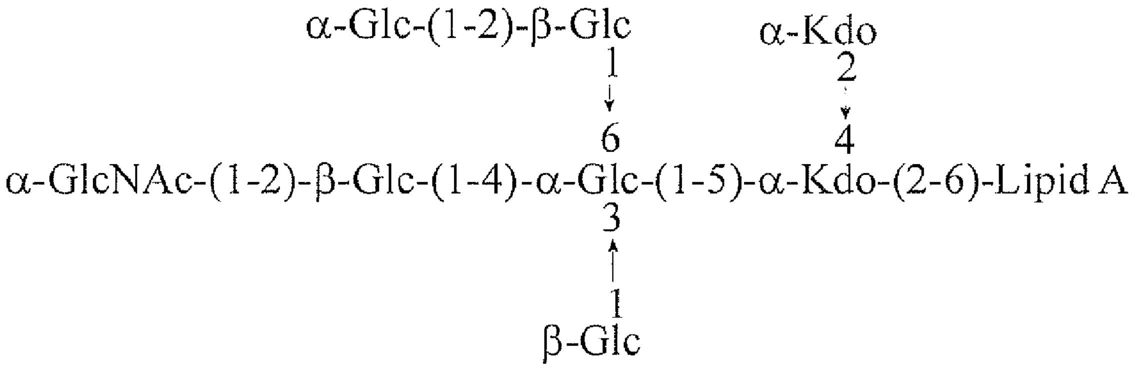
FIG. 2 Structure of the LPS from the lgt2 mutant of serotype A strain of *Moraxella catarrhalis*

Our ultimate goal was to produce an LPS-based vaccine against Mc and our initial goal was to identify inner core structures that would be conserved across the range of *Moraxella* strains and illustrate that these inner core epitopes were capable of eliciting an immune response which could recognise and facilitate killing of wild-type strains. Our rationale was to prepare a mutant strain of Mc that contained a conserved inner core structure, which did not elaborate the host like structures observed in the outer core LPS, that could lead to auto-immunity due to their mimicry of structures found on human cells. Peak et al FEBS J 2007 v 274, p 2024-37 had identified a glycosyltransferase they termed lgt2 in a serotype A strain, resulting in a truncated structure, which we postulated may be a sufficiently conserved inner structure to afford protection against all three serotypes (FIG. 2). The subsequent examples detail our production of the lgt2 mutant in which the conserved structure is elaborated. We will then give details of the production of monoclonal antibodies to this conserved structure and illustrate their cross-reactivity and ability to protect. Finally we will detail a structure which lacks the terminal N-acetyl glucosamine residue, by virtue of preparing a lgt2/lgt4 double mutant, that we believe will present the conserved inner core structure optimally.

We therefore initially mutated the lgt2 gene in order to examine this truncated structure as a candidate vaccine antigen.

Example 2

Lgt2 Mutant Construction and Characterisation

The lgt2 mutant was created by the insertion of an antibiotic-resistance cassette in the lgt2 gene and core oligosaccharide from the lgt2 mutant was examined by NMR, with the assignment consistent with the predicted lgt2 core OS structure (Table 1).

Figure 3:
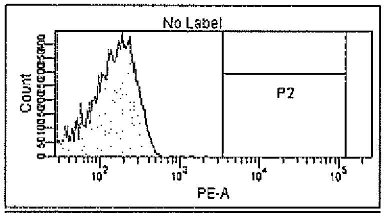
FIG. 3. FACS analysis of binding of antibodies as indicated to whole cells of *Moraxella catarrhalis* or *Neisseria meningitidis* as indicated.
Figure 3:
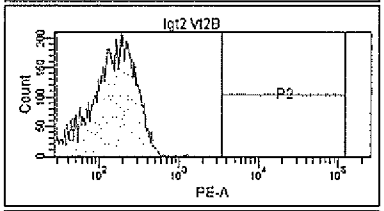
Figure 3:
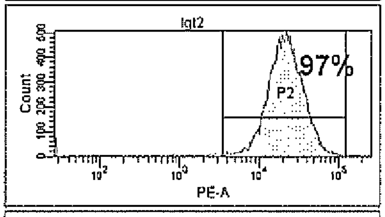
Figure 3:
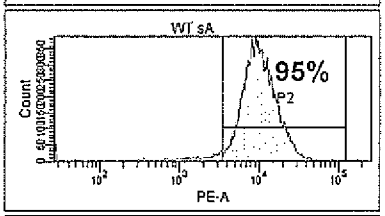
Figure 3:
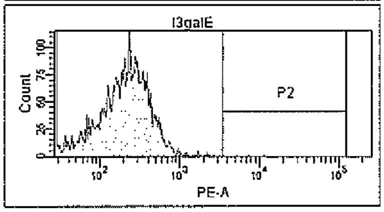

Example 3 mAb Production and Cross-Reactivity mAb MC2-1 was generated to Mc lgt2 killed whole cells and selected by screening with lgt2 and wt LPS. The specificity of mAb MC2-1 was examined by FACS and was found to recognise Mc cells specifically and did not cross-react with meningococcal cells, thus illustrating the specificity of the mAb, so that the possibility of unwanted non-specific cross-reactivity can be ruled out (FIG. 3).

Figure 4:
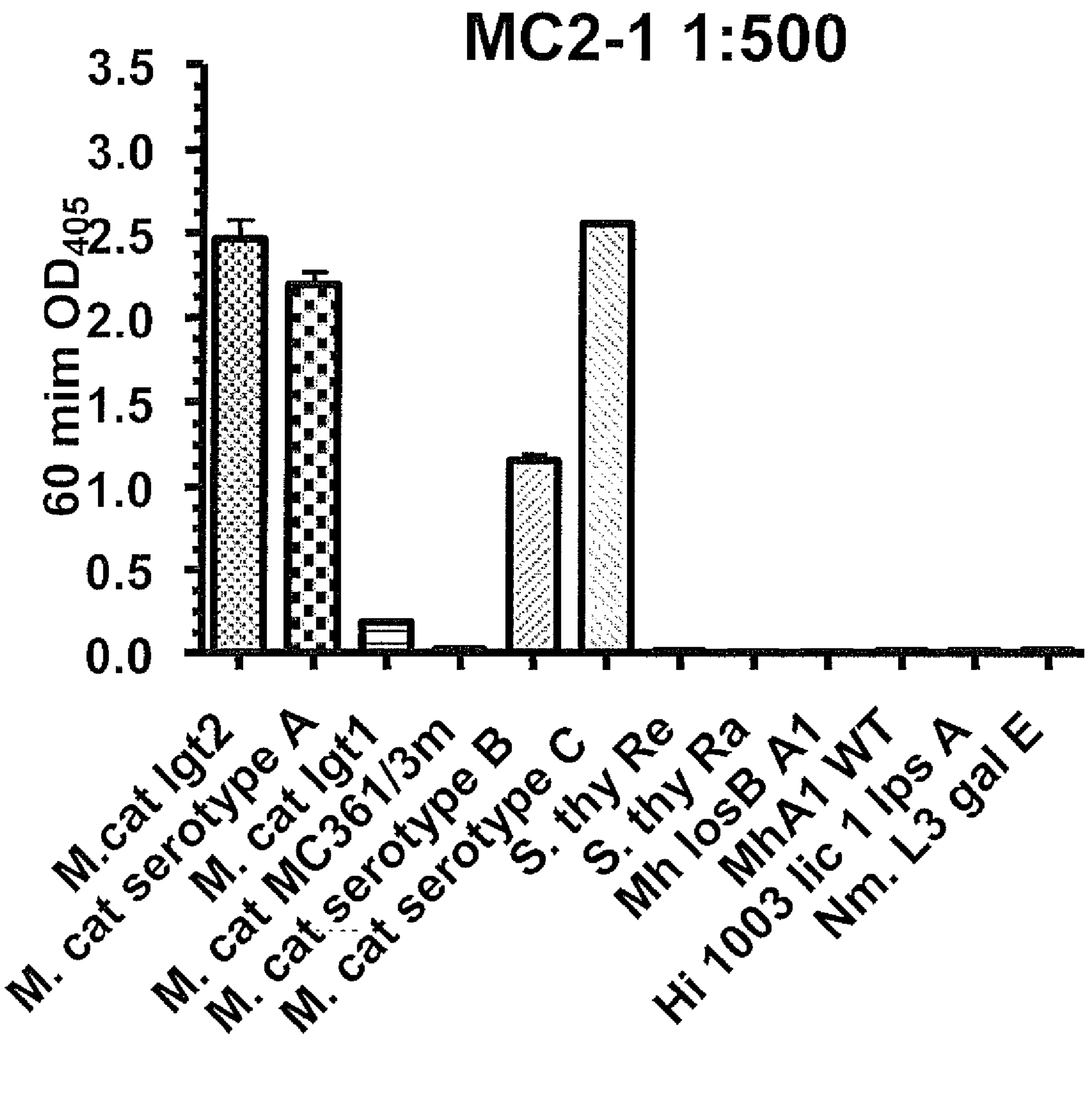
FIG. 4. LPS ELISA analysis of cross-reactivity of mAb MC2-1 against *Moraxella catarrhalis* (M. cat), *Salmonella*

Subsequently the ability of mAb MC2-1 to recognise serotypes B and C was also examined by LPS ELISA and illustrated that mAb MC2-1 was capable of recognising all three serotypes, revealing the potential of this inner core structure as a vaccine antigen (FIG. 4).

Furthermore, we examined *Moraxella* strains lgt1 and MC361/3m that elaborate LPS molecules that are more truncated than the lgt2 mutant, and these are not recognised by MC2-1. MC2-1 specificity is also shown as other bacterial species (*Salmonella typhimurium, Mannheimia haemolytica, Haemophilus influenzae* and *Neisseria meningitidis*) are not recognised. This once again illustrates the specificity of the mAb, so that the possibility of unwanted non-specific cross-reactivity can be ruled out, such that we know we are effectively targeting *Moraxella* cells.

Example 4 mAb MC2-1 Bactericidal Activity

MAb MC2-1 was bactericidal against wild type serotype A. (FIG. 5).

Example 5

New mAb Production

A second series of mAbs were raised to this lgt2 structure by the same standard methodology as used in Example 3. Cross-reactivity screening of the candidate mAbs obtained revealed a strong immunodominance of the terminal GlcNAc residue of the core OS (FIG. 6).

Ascites fluid was raised to mAbs MC2-10 and -15 and the ascites fluid was titrated against LPS from the lgt2 mutant and serotypes A and C (FIG. 7).

The ascitic fluid was subsequently tested for their ability to recognise whole cells of *Moraxella catarrhalis* (FIG. 8), and was then tested in a bactericidal assay which revealed killing of the homologous strain and of the wild-type strain (Table 2).

Example 6

Lgt2/4 Mutant Construction and Characterisation

As the terminal GlcNAc residue of the core OS appeared to be a somewhat dominant epitope, a double mutant lgt2/lgt4 was prepared that lacks the GlcNAc residue, which could lead to an improved cross-reactive response. This structure is common to all three Mc serotypes (FIG. 9) and was confirmed by NMR spectroscopy (Table 3).

While the preferred embodiments of the invention have been described above, it will be recognized and understood that various modifications may be made therein, and the appended claims are intended to cover all such modifications which may fall within the spirit and scope of the invention.

TABLE 1

$^1H$ & $^{13}C$ NMR data for the *Moraxella catarrhalis* serotype A lgt2 mutant α-Glc-(1-2)-β-Glc
1
↓
6
α-GlNAc-(1-2)-β-Glc-(1-4)-α-Glc-(1-5)-α-Kdo
3
↑
1
β-Glc

| Residue | H-1/(C-1) | H-2/(C-2) | H-3/(C-3) | H-4/(C-4) | H-5/(C-5) | H-6/(C-6) |
|---|---|---|---|---|---|---|
| 3,4,6-α-Glc | 5.14 | 3.90 | 4.51 | 3.96 | 4.60 | 4.13, 4.03 |
| | (99.7) | (73.7) | (75.3) | (73.7) | (70.0) | (67.8) |
| t-β-Glc | 5.07 | 3.34 | 3.52 | 3.36 | 3.51 | nd |
| | (102.4) | (73.9) | (75.7) | (69.9) | (75.8) | |
| 2-β-G1c- > 4 | 5.20 | 3.38 | 3.59 | 3.46 | 3.49 | 3.82, 3.74 |
| | (97.5) | (81.2) | (74.7) | (69.7) | (75.8) | (63.2) |
| 2-β-Glc- > 6 | 4.61 | 3.49 | 3.56 | 3.42 | 3.42 | nd |
| | (102.7) | (75.8) | (76.2) | (69.7) | (75.8) | |
| t-α-GlcNAc | 5.09 | 4.03 | 3.73 | 3.57 | 3.81 | nd |
| | (99.0) | (53.9) | (72.0) | (69.8) | (71.5) | |
| t-α-Glc | 5.41 | 3.38 | 3.75 | 3.99 | 3.84 | nd |
| | (96.7) | (71.8) | (72.9) | (72.0) | (71.5) | |

TABLE 2

Bactericidal titers[1] of mouse monoclonal antibodies raised against *Moraxella catarrhalis* stain lgt2 against serotype A wt and lgt2 mutant strains. Baby rabbit complement (⅛ dilution) was used.

| mAb/Strain | Mc wt | Mc lgt2 |
|---|---|---|
| MC2-10 | <5 | **<u>>1000</u>**[2] |
| MC2-15 | <5 | <5 |
| +ve control[3] | nd | **<u>>10</u>** |

[1]Bactericidal titers expressed as the reciprocal of the serum dilution yielding >=50% bactericidal killing when compared to the no antibody control.
[2]Titers in bold and underlined illustrate bactericidal killing.
[3]Positive control was mouse monoclonal antibody MC2-1

TABLE 3

$^1H$ & $^{13}C$ NMR data for the *Moraxella catarrhalis* serotype A lgt2/lgt4 double mutant α-Glc-(1-2)-β-Glc
1
↓
6
β-Glc-(1-4)-α-Glc-(1-5)-α-Kdo
3
↑
1
β-Glc

| Residue | H-1/(C-1) | H-2/(C-2) | H-3/(C-3) | H-4/(C-4) | H-5/(C-5) | H-6/(C-6) |
|---|---|---|---|---|---|---|
| 3,4,6-α-Glc | 5.27 | 3.83 | 4.42 | 4.04 | 4.33 | 4.22 |
| | (99.4) | (73.8) | (75.2) | (74.0) | (70.0) | 4.16 |
| | | | | | | (67.2) |
| t-β-Glc- > 3 | 5.02 | 3.34 | 3.51 | 3.40 | 3.51 | nd |
| | (101.2) | (73.4) | (75.9) | (69.7) | (75.9) | |
| t-β-Glc- > 4 | 4.70 | 3.33 | 3.48 | 3.35 | 3.43 | nd |
| | (101.4) | (73.4) | (75.8) | (73.4) | (75.8) | |

TABLE 3-continued $^1H$ & $^{13}C$ NMR data for the *Moraxella catarrhalis* serotype A lgt2/lgt4 double mutant

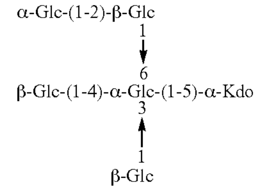

| Residue | H-1/(C-1) | H-2/(C-2) | H-3/(C-3) | H-4/(C-4) | H-5/(C-5) | H-6/(C-6) |
|---|---|---|---|---|---|---|
| 2-β-Glc | 4.64 (103.0) | 3.48 (75.8) | 3.57 (76.3) | 3.49 (69.8) | 3.43 (75.7) | nd |
| t-α-Glc | 5.39 (97.6) | 3.58 (72.7) | 3.75 (72.4) | 4.04 (71.7) | 3.80 (72.8) | nd |

The invention claimed is:

1. An isolated lipopolysaccharide moiety of a lgt2/lgt4 double mutant of *Moraxella catarrhalis*, wherein the lipopolysaccharide moiety consists essentially of a conserved penta-glucosyl inner core moiety having the structure:

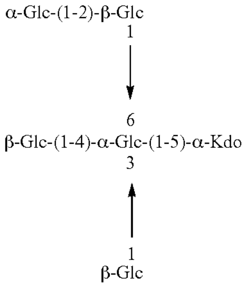

wherein the Kdo is 2-keto-3-deoxy-octulosonic acid and the Glc is glucose.

2. A composition comprising the isolated lipopolysaccharide moiety of claim 1.

3. A glycoconjugate comprising an isolated lipopolysaccharide moiety of a lgt2/lgt4 double mutant of *Moraxella catarrhalis* and an immunogenic carrier, wherein the lipopolysaccharide moiety consists essentially of a conserved penta-glucosyl inner core moiety having the structure:

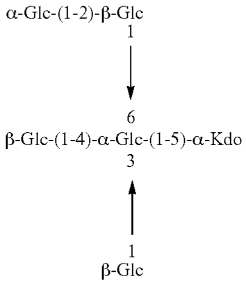

wherein the Kdo is 2-keto-3-deoxy-octulosonic acid and the Glc is glucose.

4. The glycoconjugate according to claim 3, wherein the lipopolysaccharide moiety and the immunogenic carrier are cross-linked with a linker molecule.

5. An isolated lipopolysaccharide moiety consisting of a conserved penta-glucosyl inner core moiety having the structure:

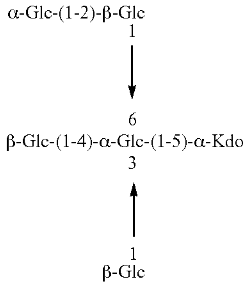

wherein the Kdo is 2-keto-3-deoxy-octulosonic acid and the Glc is glucose.

6. A glycoconjugate comprising an isolated lipopolysaccharide moiety and an immunogenic carrier, wherein the lipopolysaccharide moiety consists of a conserved penta-glucosyl inner core moiety having the structure:

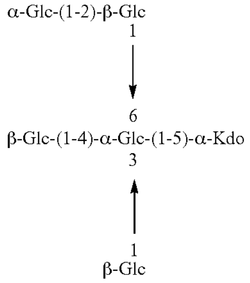

wherein the Kdo is 2-keto-3-deoxy-octulosonic acid and the Glc is glucose.

* * * * *